United States Patent [19]

Hechter

[11] Patent Number: 4,975,286

[45] Date of Patent: Dec. 4, 1990

[54] AQUEOUS CATHARTIC SOLUTION

[75] Inventor: Herbert G. Hechter, Glen Cove, N.Y.

[73] Assignee: E-Z-EM, Inc., Westbury, N.Y.

[21] Appl. No.: 352,041

[22] Filed: May 15, 1989

Related U.S. Application Data

[63] Continuation-in-part of Ser. No. 71,868, Jul. 10, 1989, abandoned.

[51] Int. Cl.$^5$ ............................................. A61K 33/06
[52] U.S. Cl. ................................... 424/682; 424/709; 424/717; 424/722
[58] Field of Search ............... 424/663, 709, 682, 717, 424/722

[56] References Cited

PUBLICATIONS

Girard et al—AJR 142, Jun. 1984, 1147–1149.

Handbook of Nonprescription Drugs, Fifth Ed., pp. 43–44, American Pharmaceutical Assoc., Wash. D.C.
Golytely, Peg Electrolyte Gastrointestinal Lavage Solution, Hospital Formulary Monograph.

*Primary Examiner*—Frederick E. Waddell
*Attorney, Agent, or Firm*—McAulay, Fisher, Nissen & Goldberg

[57] ABSTRACT

An aqueous cathartic solution and method for bowel cleansing is provided. The solution is isotonic, has a minimum buffering effect on human blood and is substantially inorganic. The aqueous solution includes about 3.5 grams/liter of sodium sulfate; about 4.82 grams/liter of magnesium sulfate; about 1.9 grams/liter of sodium bicarbonate; about 3.85 grams/liter of sodium chloride; about 0.746 grams/liter of potassium chloride. To cleanse the bowel between 3.0 and 4.0 liters of the solution are usually administered to a patient.

18 Claims, No Drawings

AQUEOUS CATHARTIC SOLUTION

BACKGROUND OF THE INVENTION

This is a Continuation In Part of Application Ser. No. 071,868 filed on July 10, 1987, now abandoned.

The present invention relates to an aqueous cathartic solution for bowel cleansing and more particularly to such a solution for bowel cleansing prior to colonoscopy or barium enema x-ray examination.

It is known in the art that thorough cleansing of the bowel is needed before either a colonoscopy or a barium enema x-ray examination. To perform either of these diagnostic examinations, the bowel should be free of fecal matter and substantially dry.

Many different regimens for cleansing of the bowel are used. Most of these regimens require the ingestion of oral cathartic agents or a solution followed by the administering of cleansing enemas. The use of the cleansing enemas creates both additional discomfort for the patient and additional work for the physician or other medical personnel administering the tests.

Many of these prior art regimens use organic substances and/or polyethylene glycol. Polyethylene glycol often is not well tolerated by patients, causes the development of reflectance on the mucus membranes of the colon, creates wetness in the folds of the colon and irritation in the anal area. The presence of polyethlene glycol in prior art lavage solutions destroys cell membranes and thus these solutions do not allow harvesting of intact exfoliated cells for subsequent cytological examination. The organic constituents used in some of these regimens, when metabolized, may create explosive materials which have exploded during certain procedures causing death to the patients.

Patient tolerance is an important factor in choosing an appropriate bowel cleansing regimen. Since in lavage regimens the consumption of large quantities of solution is difficult, it is desirable to keep the quantities which must be consumed as small as possible. Further, the palatability of the solution must be considered. For example, certain prior art regimens use an orally administered solution of epsom salts and carbonated water. This solution was not well tolerated because of its taste.

An orally administered solution should have little or no effect on blood physiology, osmolarity, pH and ion concentrations. This avoids physiological change.

Without proper bowel cleansing, examinations to determine the existence of colorectal diseases and abnormalities, such as malignancies, cannot be done effectively. The foregoing is significant since colorectal cancer is a serious health problem in the United States and other parts of the world. It is presently estimated that in people over the age of 40, one in every one thousand will develop colorectal cancer. It is known that the early detection of such colorectal cancer significantly increases survival rates and further that such early diagnosis enables treatment with less drastic surgical intervention. Additionally, with a lavage solution that does not damage cells, it may be possible to collect an effluent with intact cells which can be harvested for subsequent cytological analysis.

It is an object of the present invention to provide an aqueous, orally administered cathartic solution which cleanses the bowel sufficiently to avoid the need of cleansing enemas.

It is another object of this invention to provide such a solution which contains substantially no organic components.

Still a further object of this invention is to provide such a solution which prevents the development of reflectance on the mucus membranes of the colon and which further prevents wetness in the folds of the colon.

Another object of this invention is to provide such a solution which does not adversely effect the body physiology and chemistry.

Yet another object of this invention is to provide such a solution which has maximal cathartic effect with minimal volume intake.

Another object of this invention is to provide such a solution which does not damage cell membranes so that the solution may be used to obtain cells for a cytological examination.

BRIEF DESCRIPTION

In one embodiment of the invention an aqueous cathartic solution for bowel cleansing is provided. The aqueous solution is substantially inorganic, isotonic and has a minimal buffering effect on body fluids. The aqueous solution contains, in concentrations substantially similar to their concentrations in human blood, sodium ions and bicarbonate ions. It contains chloride ions in concentrations lower than the concentration of chloride ions in human blood, potassium ions in concentrations higher than the concentration of potassium ions in human blood and magnesium and sulfate ions in concentrations to provide significant cathartic effect. The cathartic solution has a maximal, safe, cathartic effect with a minimal intake of solution. It cleanses the bowel thoroughly enough so that the colonoscopy or barium enema x-ray examination can be done without the need of cleansing enemas and provides sufficient intact exfoliated colon cells to permit cell harvesting for cytological examination.

DETAILED DESCRIPTION

In a preferred embodiment of the present invention, an inorganic, isotonic, aqueous cathartic solution is provided. This solution contains about 3.5 grams per liter of sodium sulfate; about 4.82 grams per liter of magnesium sulfate; about 1.9 grams per liter of sodium bicarbonate; about 3.85 grams per liter of sodium chloride; and about 0.746 grams per liter of potassium chloride. The solution has a minimal buffering effect on body fluids, has a low absorption through the intestinal tract and avoids excessive irritation of the intestinal walls and does not damage intestinal cells.

The solution of the present invention provides sodium and bicarbonate ions in concentrations substantially similar to their concentration in human blood, potassium ions in concentrations higher than their concentration in human blood, chloride ions in concentrations lower than their concentration in human blood, and magnesium and sulfate ions in concentrations to provide significant cathartic effect. The ionic concentration of the solution prevents adverse effects on body physiology and chemistry caused by ingestion of the solution by providing the solution with its isotonic nature and its ability to have a minimal buffering effect.

The ionic makeup of the cathartic solution of the present invention avoids any interference with the major physiological mechanisms of the body. Since sodium ions are among the most abundantly osmotic active ions in the body's extracellular fluid, any substantial change in the concentration of these ions would effect the volume of the extracellular fluid, resulting in hydration.

The concentration of bicarbonate ions in body fluids helps keep the pH of the fluids stable. Any substantial change in the concentration of bicarbonate ions can lead to respiratory changes resulting in respiratory acidosis, metabolic acidosis or renal problems.

To avoid renal or cardiac problems it is important to avoid lowering the physiologic concentration of potassium ions or raising the physiologic concentration of chlorides.

Magnesium and sulfate ions in proper concentrations act as cathartic agents. The concentrations must be such as to avoid any toxic effects.

Although the concentrations of these essential ions differ in different body fluids, in blood serum these concentrations in milloequivalents per liter are about: 131 to 147 for sodium ions; 3 to 5 for potassium ions; 6 to 10 for calcium ions, magnesium ions, or a combination of calcium and magnesium ions; 97 to 109 for chloride ions; 21 to 30 for bicarbonate ions.

Although our preferred embodiment of the present invention is indicated above, it should be noted that the concentration of constituents can be varied in view of the above range of blood serum ion concentrations. Accordingly, the solution of the present invention, in milloequivalents per liter, may have the following ionic concentration ranges: 125 to 152 for sodium ions; 72 to 88 for magnesium ions; 68 to 83 for chloride ions; 20 to 25 for bicarbonate ions. Because physiological effect and concentration of magnesium and calcium ions as serum are similar, the cathartic solution may also have a calcium containing a compound such as calcium chloride. It is most important to keep the concentration of potassium ions in the solution low.

The magnesium and sulfate ions of the solution provide maximal cathartic effect. The overall ionic mixture provides minimal disturbance to body chemistry.

In order to effectively cleanse the bowel between three to 4 liters of the aqueous cathartic solution of the present invention must be ingested by the patient. The solution is generally ingested the night before the colonoscopy or barium enema examination. This volume of solution cleans the bowels sufficiently to make cleansing enemas unnecessary. It has been further found that a clear effluent collected after cleansing of the bowel with this solution contains sufficient intact exfoliated cells to allow cell harvesting for cytological examination.

It has been found that the most efficient bowel cleansing occurs if the cathartic solution of the present invention is prepared and ingested in the following manner.

Approximately sixty (60) grams of a dry power formulation is provided in a four (4) liter container. About twenty-four (24) hours prior to the examination procedure a liter of lukewarm tap water is mixed with the dry power contents in the container. After this initial mixing, three (3) additional liters of tap water are added to the container and the entire solution is mixed again. To aid in patient tolerance the mixed solution is chilled.

The patient may have a light lunch at about 1:00 P.M. on the day before the procedure. After this the patient may not drink or eat anything other than what is set forth in the regimen.

At about 3:00 P.M. in the afternoon the patient should take about 30 milligrams of bisacodyl. The bisacodyl is generally provided in tablet form. The tablets should be swallowed whole. At about 7 P.M. eight (8) ounces of the chilled solution should be ingested. Although the patient may rinse his mouth with tap water, no tap water should be swallowed. At ten (10) minute intervals, additional eight (8) ounce portions of the solution should be ingested until a total of two (2) liters of solution has been ingested. The patient should consume no solution for a ninety (90) minute period and then continue to drink eight (8) ounce portions of solution at ten (10) minute intervals until the entire solution has been ingested.

Although four liters is the preferred dosage, patients drinking average dosage amounts of between 1.6 liters and 2.8 liters of solution had their colons cleared sufficiently for a colonoscopy.

When the solution of the present invention is ingested in this manner it has been found that the colon is cleansed sufficiently to permit colonoscopy and endoscopy. It further has been found that the solution of the present invention is better tolerated by patients than prior art solutions. When the solution of the present invention is used there is no need for cleansing enemas, which are often needed with other lavage solutions to insure adequate cleansing. Further the colonic effluent collected has sufficient amounts of intact exfoliated colonic cells to permit cytological examination. The presence of polyethylene glycol in prior art solutions is believed to limit the amount of intact exfoliated cells in the effluent because the polyethylene glycol punctures the cell membrane.

In contrast to prior art bowel cleansing regimens, the solution of this invention does not impart substantial reflectance to the mucus membranes of the colon wall, does not result in substantial wetness of the colon, and is less of an irritant to lesions in the colon and anal regions. Because of the solution of the present invention contains substantially no organic matter, there is no problem with development of potentially explosive gases.

The solution of the present invention has led to surprising, medically significant results. Despite providing a more palatable and better tolerated solution the present invention provides such a solution which cleans better, at lower doses, than prior art solutions. Further the solution of the present invention allows for the harvesting of exfoliated colonic cells and the subseqauent cytological examinatin of these cells.

What is claimed is:

1. An aqueous solution for cleansing of the bowel consisting essentially of:
   sodium ions and bicarbonate ions in concentrations substantially similar to the construction of these ions of human blood;
   chloride ions in concentrations lower than the concentration of chloride ions in human blood;
   potassium ions in concentrations higher than the concentration of potassium ions in human blood;
   sulfate ions;
   magnesium ions in concentrations to cause significant cathartic effect;
   said solution being substantially inorganic;
   said solution being isotonic; and
   said solution causing a minimum exchange of cations and anions from the gastrointestinal tract into the blood.

2. The solution of claim 1 wherein there are between about 125 to 152 mEq. of sodium ions per liter of solution.

3. The solution of claim 1 wherein there are between about 72 to 88 mEq. of magnesium ions per liter of solution.

4. The solution of claim 1 wherein there are between about 68 to 83 mEq. of chloride ions per liter of solution.

5. The solution of claim 1 wherein there are between about 20 to 25 mEq. of bicarbonate ions per liter of solution.

6. The solution of claim 1 wherein there are between about 9 to 11 mEq. of potassium ions per liter of solution.

7. The solution of claim 1 wherein there are between about 117 to 141 mEq. of sulfate ions per liter of solution.

8. The solution of claim 1 having an osmolarity of between about 260 to 300 milliosmomoles per kilogram.

9. The solution of claim 1 wherein there are between about 125 to 152 mEq. of sodium ions per liter of solution, between about 72 to 88 mEq. of magnesium ions per liter of solution, between about 68 to 83 mEq. of chloride ions per liter of solution, between about 20 to 25 mEq. of bicarbonate ions per liter of solution, between about 9 to 11 mEq. of potassium ions per liter of solution, and between about 117 to 131 mEq. of sulfate ions per liter of solution.

10. An aqueous cathartic solution for cleansing of the bowel comprising:
   about 3.5 grams/liter of sodium sulfate;
   about 4.82 grams/liter of magnesium sulfate;
   about 1.9 grams/liter of sodium bicarbonate;
   about 3.85 grams/liter of sodium chloride;
   about 0.746 grams/liter of potassium chloride;
   said solution being substantially inorganic;
   said solution having a minimal buffering effect on body fluids; and
   said solution being isotonic.

11. The solution of claim 1 wherein said solution has a minimal effect on blood physiology, minimal absorption from the intestinal tract, and is minimally irritating to the intestinal wall.

12. The solution of claim 9 wherein said solution has a minimal effect on blood physiology, minimal absorption from the intestinal tract, and is minimally irritating to the intestinal wall.

13. A method of cleansing the bowel comprising orally administering to a patient about 3.0 to 4.0 liters of the aqueous cathartic solution of claim 1.

14. A method of cleansing the bowel comprising orally administering to a patient about 3.0 to 4.0 liters of the aqueous cathartic solution of claim 9.

15. A method of cleansing the bowel comprising orally administering to a patient about 3.0 to 4.0 liters of the aqueous cathartic solution of claim 10.

16. A method of cleansing the bowel the method comprising the steps:
   preparing 4.0 liters of the aqueous cathartic solution of claim 1;
   ingesting about 30 milligrams of bisacodyl;
   ingesting eight (8) ounces of said aqueous cathartic solution about four hours subsequent to ingestion of said bisacodyl;
   at ten minute intervals, subsequent to the ingestion of said eight ounces of aqueous cathartic solution, ingesting further eight ounce portions of said aqueous cathartic solution until a total of two liters of said solution has been ingested;
   approximately ninety minutes subsequent to ingestion of the last eight ounce portion of aqueous cathartic solution ingesting an additional eight ounce portion of aqueous cathartic solution;
   at ten minute intervals subsequent to ingesting said additional eight ounce portion of aqueous cathartic solution ingesting still further eight ounce portions of agueous cathartic solution until four liters of said solution has been ingested.

17. The method of claim 16 wherein the bisacodyl is ingested the afternoon prior to a morning procedure.

18. The method of claim 16 wherein the person ingesting the aqueous cathartic solution may have nothing to eat or drink, other than the aqueous cathartic solution and the bisacodyl, after 1 P.M. of the afternoon prior to the procedure.

* * * * *